United States Patent [19]
Phillion et al.

[11] Patent Number: 5,482,974
[45] Date of Patent: Jan. 9, 1996

[54] SELECTED FUNGICIDES FOR THE CONTROL OF TAKE-ALL DISEASE OF PLANTS

[75] Inventors: Dennis P. Phillion; Karey A. Van Sant, both of St. Charles; Daniel M. Walker, St. Louis, all of Mo.

[73] Assignee: Monsanto Company, St. Louis, Mo.

[21] Appl. No.: 207,508

[22] Filed: Mar. 8, 1994

[51] Int. Cl.[6] .................. A01N 37/18; A01N 33/06; C07C 233/65
[52] U.S. Cl. .................. 514/619; 514/622; 564/163; 564/176
[58] Field of Search .................. 514/622, 619; 564/176, 163

[56] References Cited

U.S. PATENT DOCUMENTS

| | | | |
|---|---|---|---|
| 4,060,637 | 11/1977 | Stenger et al. | 424/324 |
| 4,228,165 | 10/1980 | Ogata et al. | 424/248.5 |
| 4,248,869 | 2/1981 | Ogata et al. | 424/248.5 |
| 4,485,105 | 11/1984 | Shepherd | 424/248.5 |
| 4,892,948 | 1/1990 | Nishihira et al. | 544/326 |
| 4,997,836 | 3/1991 | Sugihara et al. | 514/253 |
| 4,999,381 | 3/1991 | Crowley et al. | 514/618 |
| 5,037,982 | 8/1991 | Nishihira et al. | 544/326 |
| 5,053,073 | 10/1991 | Anthony et al. | 71/94 |
| 5,283,352 | 2/1994 | Bäckström et al. | 558/401 |

FOREIGN PATENT DOCUMENTS

| | | |
|---|---|---|
| 0538231 | 4/1993 | European Pat. Off. . |
| 63-284164 | 11/1988 | Japan . |

OTHER PUBLICATIONS

Doadt et al. Tetrahedron Letters 26 (9) pp. 1149–1152 (1985).
Carpenter et al. Org. Chem. 50 (22) pp. 4362–4368 (1985).
Nishimoto et al. Chem. Abstracts vol. 101, No. 19, 170383y (1984).
White et al., Thiophene Carboxamide Fungicides, Pest. Biochem., 25, 188–204 (1986).
Eiglsperger, A., et al. "The Enantiomers of N,N–Dimethylthiobenzamides: Chromatographic Behavior and Rotational Barriers." J. of Molecular Structure, 126: 421–432, 1985. (cont'd).
Fitt, J. J., et al. "Ortho Lithiation of Thiobenzamides." J. of Organic Chemistry, 41(25): 4029–4031, 1976.
Fu, J. M., et al. "The Directed Ortho Metalation Connection to Aryl–Aryl Cross Coupling. A General Regiospecific Synthesis of Phenanthrols." Tetrahedron Letters, 29(43): 5459–5462, 1988.
Grimshaw, J., et al. "Electrochemical Reactions. Intermolecular Radical Substitution During the Reduction of 2–Halo–N–methylbenzamides." J. of Chem. Soc., Perkin Trans. 1, No. 22, pp. 2448–2455, 1977.
McDonald, J. E., et al. "An Anomalous Metalation of a Trimethylsilyl Group." Tetrahedron Letters, 28(17): 1851–1852, 1987.
Mills, R. J., et al. "Directed Ortho Metalation of N,N–Diethylbenzamides. Silicon Protection of Ortho Sites and the o–Methyl Group," J. of Organic Chemistry, 54: 4372–4385, 1989. [Mills I].
Mills, R. J., et al. "Dilithiated Synthons of Tertiary Benzamides, Phthalamides, and O,O'–Aryl Dicarbamates." Tetrahedron Letters, 26(9): 1145–1148, 1985. [Mills II].
Reuvers, A. J. M., et al. "Chemistry of Neopentyl Derivatives–II. Restricted Rotation in 2,6–Disubstituted Neopentylbenzenes." Tetrahedron, 27: 3713–3721, 1971.
Salituro, F. G., et al. "Facile Synthesis of L–Kynurenine." J. of Organic Chemistry, 53(26): 6138–6139, 1988.
Sandifer, R. M., et al. "Silation at the ortho position of N–methyl and N–phenylbenzamide." Chemistry and Industry, 19 Mar. 1977.
Slocum, D. W., et al. "Directed Metallation of Model Adrenaline Compounds." J.C.S. Chem. Comm., pp. 268–269, 1974.
Snieckus, Victor. "Directed Ortho Metalation. Tertiary Amide and O–Carbamate Directors in Synthetic Strategies for Polysubstitued Aromatics." Chemical Reviews, vol. 90, No. 6, 1990.
Takahasi, Y., et al. "Application of the ORMUCS Method to Structure–Activity Studies on the Fungicidal Activity of (List continued on next page.)

*Primary Examiner*—Glennon H. Hollrah
*Assistant Examiner*—Mary C. Cebulak
*Attorney, Agent, or Firm*—Joan Thierstein

[57] ABSTRACT

A compound for controlling Take-all disease of plants by applying, preferably to the seed prior to planting, a fungicide of the formula

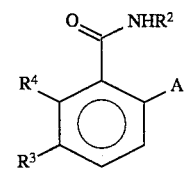

wherein $R^2$ is ethyl, iso-propyl, propyl or allyl;

A is $N(CH_3)_{1-n}H_nR^5$ or $OR^6$ wherein n is 0 or 1, $R^5$ is $(CH_3)_m(CH_3CH_2)_{3-m}C$, 1-methylcyclopentyl, 1-methylcyclohexyl or 2,3-dimethyl-2-butyl wherein m is 0, 1, 2 or 3 and $R^6$ is independently $R^5$ or 2,3,3-trimethyl-2-butyl;

$R^3$ is H or independently $R^4$; and $R^4$ is halo or $CH_3$;

with the proviso that when A is $N(CH_3)_{1-n}H_nR^5$, if $R^3$ is H and $R^5$ is 1-methyl-1-cyclohexyl or $(CH_3)_m(CH_2CH_3)_{3-m}C$, where m is 0 or 3, or if $R^3$ is halo and $R^5$ is $(CH_3)_m(CH_3CH_2)_{3-m}C$, where m is 3, then $R^2$ cannot be ethyl;

and with the proviso that when A is $OR^6$ then m is equal to or less than 2, and if $R^3$ is H or halo and $R^2$ is ethyl or isopropyl, then $R^6$ is $(CH_3)_m(CH_3CH_2)_{3-m}C$ where m is 1; or an agronomic salt thereof compositions, methods of use and processes of preparation therefor.

12 Claims, No Drawings

OTHER PUBLICATIONS

Mepronil Derivatives." Quant. Struct.–Act. Relat. 6(1): 17–21, 1987.
Pepin, et al. Chemical Abstract: 114:96801h, Feb. 1991.
Pepin, et al. Chemical Abstract: 113:78409m, Mar. 1990.
Lacova, et al. Chemical Abstract: 110:231500u, Feb. 1987.
Fischer, et al. Chemical Abstract: 106:18386x, Jan. 1986.
Pavanetto, et al. Chemical Abstract: 103:101888w, Jun. 1985.
Montanari, et al. Chemical Abstract: 102:19477g, Feb. 1984.
Metzner, et al. Chemical Abstract: 91:187234y, Apr. 1979.
Ogata, et al. Chemical Abstract: 91:74332k, Apr. 1979.

SELECTED FUNGICIDES FOR THE CONTROL OF TAKE-ALL DISEASE OF PLANTS

FIELD OF THE INVENTION

This invention relates to certain substituted benzamide compounds and processes for the preparation thereof, which are novel, a method for the control of Take-All disease in plants, particularly cereals, by the use of the compounds, and fungicidal compositions for carrying out the method.

BACKGROUND OF THE INVENTION

Take-All disease is a serious problem in the production of cereals, particularly wheat and barley. It is caused by the soil-borne fungus *Gaeumannomyces graminis* (Gg). The fungus infects the roots of the plant, and grows throughout the root tissue, causing a black rot. The growth of the fungus in the roots and lower stem prevents the plant from obtaining sufficient water and/or nutrients from the soil, and is manifested as poor plant vigor and, in severe instances of disease, by the formation of "whiteheads," which are barren or contain few, shriveled grains. Yield losses result. Gaeumannomyces species also infect other cereal crops, for example, rice and oats; and turf.

Currently the primary means of avoiding crop loss due to infestation of the soil by Gg has been to rotate the crop grown to one which is resistant to Gg. However, in areas where the primary crops are cereals, rotation is not a desirable practice, and an effective control agent is greatly desired.

It is an object of this invention to provide compounds that provide superior and unexpected control of the growth of Gg in the soil so as to reduce crop loss. It is a further object of this invention to provide an effective method for superior and unexpected control of Take-all disease in plants. It is still a further object of this invention to provide fungicidal compositions that may be used for superior and unexpected control of Take-all disease.

The international patent application PCT/US92/08633 discloses a broad scope of compounds effective against Take-all disease. The present invention are selected compounds having superior and unexpected effectiveness against the present disease.

References related to the processes of the present invention are *Synth. Commun.*, 14, 621 (1984) and *Synthesis* 303, (April, 1978).

Gajda, T. and Zwierzak, A. in "Phase-Transfer-Catalysed N-Alkylation of Carboxamides and Sulfonamides" published in *Synthesis*, pp.1005–7, December 1981 and Abiko, A. et al. in "KMnO$_4$ Revisited: Oxidation of Aldehydes to Carboxylic Acids in the tert-Butyl Alcohol—Aqueous NaH$_2$PO$_4$ System" published in *Tetrahedron Letters*, Vol.27, No. 38, pp. 4637–4540, 1986 are additional references related to the processes of the present invention. Additionally, related abstracts include Derwent Abstract Nos., 87-203436/29, 89-013361/02, 90-213193/28, 91-061915/09, 93-062565/08 and 93-096743/12.

SUMMARY OF THE INVENTION

The present invention provides a compound of the formula (I)

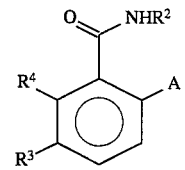

wherein $R^2$ is ethyl, iso-propyl, propyl or allyl;

A is $N(CH_3)_{1-n}H_nR^5$ or $OR^6$ wherein n is 0 or 1, $R^5$ is $(CH_3)_m(CH_3CH_2)_{3-m}C$, 1-methyl-1-cyclopentyl, 1-methyl-1-cyclohexyl or 2,3-dimethyl-2-butyl wherein m is 0, 1, 2 or 3 and $R^6$ is independently $R^5$, or 2,3,3-trimethyl-2-butyl;

$R^3$ is H or independently $R^4$; and $R^4$ is halo or $CH_3$;

with the proviso that when A is $N(CH_3)_{1-n}H_nR^5$, if $R^3$ is H and $R^5$ is 1-methyl-1-cyclohexyl or $(CH_3)_m(CH_2CH_3)_{3-m}C$, where m is 0 or 3, or if $R^3$ is halo and $R^2$ is $(CH_3)_m(CH_3CH_2)_{3-m}C$, where m is 3, then $R^2$ cannot be ethyl;

and with the proviso that when A is $OR^6$ then m is equal to or less than 2, and if $R^3$ is H or halo and $R^2$ is ethyl or isopropyl, then $R^6$ is $(CH_3)_m(CH_3CH_2)_{3-m}C$ where m is 1; or an agronomic salt thereof.

The present invention provides a method of controlling disease caused by Gaeumannomyces species in plants comprising applying to the seed, or the soil, a fungicidally effective amount of the fungicide of the formula I.

The invention also provides fungicidal compositions comprising a fungicidally effective amount of compound of the formula I and an agronomically acceptable carrier useful in said method.

A preferred embodiment of the present invention is a compound of the formula I wherein A is $N(CH_3)_{1-n}H_nC(CH_3)_m(CH_2CH_3)_{3-m}$ where n is 0 or 1 and where m is 1,2 or 3, $R^2$ is ethyl, propyl or allyl, $R^3$ is methyl and $R^4$ is chloro, as well as a composition and method of use therefor.

Another preferred embodiment of the present invention is a compound of the formula I wherein A is $OC(CH_3)_m(CH_2CH_3)_{3-m}$, wherein m is 1 or 2 or A is $OC(CH_3)_2CH(CH_3)_2$ and $R^2$ is allyl, $R^3$ is H or $CH_3$ and $R^4$ is chloro, as well as a composition and method of use therefor.

Another preferred embodiment is N-ethyl 2-[(1,1-diethylethyl)amino]-6-chlorobenzamide, N-ethyl 2-[(1,1,2-trimethylpropyl)amino]-6-chlorobenzamide, N-propyl 2-[(1,1-dimethylpropyl)amino]-6-chlorobenzamide or N-allyl 2-[(1,1-dimethylethyl)amino]-6-chlorobenzamide.

It is now found that compounds of the formula I which are highly active in in vitro assays also exhibit good results in in vivo assays in a manner consistent with soil mobility dependent upon substituents providing increasing hydrophilicity to the compound.

The present invention is also a process for the preparation of a compound of the formula I wherein A is defined as $OR^6$ and $R^6$ is as defined above, which comprises Step 1) contacting a compound of the formula (III)

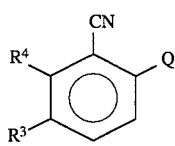

wherein Q is fluoro or chloro, and $R^3$ and $R^4$ are as defined above;

with MA in a solvent wherein M is Li, Na, or K or the equivalent of MA prepared in situ by refluxing lithium, sodium or potassium in an excess of AH wherein A is as defined above;

to obtain a compound of the formula (IV)

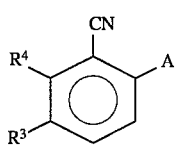

wherein A, $R^3$ and $R^4$ are as defined above; and then either

Step 2) a) heating the compound of the formula IV with NaOH, $H_2O_2$, $H_2O$ and ethanol; or, preferably, Step 2) b) refluxing the compound of the formula IV with KOH in a solvent such as alcohol or glycol and preferably tertiary-butanol or more preferably tertiary-amyl alcohol;

to obtain the compound of the formula (V)

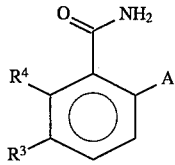

wherein A, $R^3$, and $R^4$ are as defined above;

and Step 3) treating the compound of formula V with $R^2X$ wherein X is chloro, bromo, iodo or $—OSO_2(OR^2)$ in the presence of a base, or and Step 3) treating the compound of formula V with $R^2X$ wherein $R^2$ and X is as defined above in the presence of a base and a phase transfer agent;

to obtain the compound of the formula I above wherein A is defined as $OR^6$ and $R^6$ is as defined above; or Step 2') contacting the compound of the formula IV as defined above, a) with $HAl(isobutyl)_2$ in a solvent, such as toluene or methylene chloride, and then b) with $KMnO_4$ in an alcohol solvent such as ethanol or tertiary-butanol, $KH_2PO_4$, $H_2O$, at about pH 5 to about pH 9 to obtain a compound of the formula (VI)

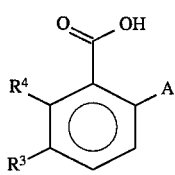

wherein A, $R^3$ and $R^4$ are as defined above, and

Step 3') treating the compound of the formula VI a) with thionyl chloride or $(COCl)_2$, in the presence of pyridine and DMF in an aprotic solvent, such as acetonitrile, methylene chloride or dichloroethane; and b) then with $H_2NR^2$ wherein $R^2$ is as defined above;

to obtain the compound of the formula I above wherein A is defined as $OR^6$ and $R^6$ is as defined above.

The present invention is also the novel compounds of the formula IV, V and VI as defined above.

Although the above processes may be carried out in one pot, i.e from the compound of the formula III to the formula I, each of the steps may also be treated to recover the product by working up each step in the usual manner. For example, a compound of the formula VI can be treated to obtain the compound of the formula I, a compound of the formula V may be treated to obtain the compound of the formula VI and a compound of the formula IV may be treated to obtain a compound of the formula V.

DETAILED DESCRIPTION OF THE INVENTION

As used herein, the term "halo" means a radical selected from chloro, bromo, fluoro, and iodo.

Control of Gg diseases, including Take-All, using a chemical control agent may be accomplished in several ways. The agent may be applied directly to soil infested with Gg, for example, at the time of planting along with the seed. Alternatively, it may be applied to the soil after planting or germination. Preferably, however, it is applied to the seed in a coating prior to planting. This technique is commonly used in many crops to provide fungicides for control of various phytopathological fungi.

Compositions of the present invention are comprised of a fungicidally effective amount of one or more of the compounds described above and one or more adjuvants. The active ingredient may be present in such compositions at levels from 0.01 to 95 percent by weight. Other fungicides may also be included to provide a broader spectrum of fungal control. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate. Stabilizers may also be used to produce stable emulsions, such as magnesium aluminum silicate and xanthan gum.

Other formulations include dust concentrates comprising from 0.1 to 60% by weight of the active ingredient on a suitable extender, optionally including other adjuvants to improve handling properties, e.g., graphite. These dusts may be diluted for application at concentrations within the range of from about 0.1–10% by weight.

Concentrates may also be aqueous emulsions, prepared by stirring a nonaqueous solution of a water insoluble active ingredient and an emulsification agent with water until uniform and then homogenizing to give stable emulsion of very finely-divided particles. Or they may be aqueous suspensions, prepared by milling a mixture of a water-insoluble active ingredient and wetting agents to give a suspension, characterized by its extremely small particle size, so that when diluted, coverage is very uniform. Suitable concentrations of these formulations contain from about 0.1–60% preferably 5–50% by weight of active ingredient.

Concentrates may be solutions of active ingredient in suitable solvents together with a surface active agent. Suitable solvents for the active ingredients of this invention for use in seed treatment include propylene glycol, furfuryl alcohol, other alcohols or glycols, and other solvents which do not substantially interfere with seed germination. If the active ingredient is to be applied to the soil, then solvents such as N,N-dimethylformamide, dimethylsulfoxide, N-methylpyrrolidone, hydrocarbons, and water-immiscible ethers, esters, or ketones.

The concentrate compositions herein generally contain from about 1.0 to 95 parts (preferably 5–60 parts) active ingredient, about 0.25 to 50 parts (preferably 1–25 parts) surface active agent and where required about 4 to 94 parts solvent, all parts being by weight based on the total weight of the concentrate.

For application to the soil at the time of planting, a granular formulation may be used. Granules are physically stable particulate compositions comprising at least one active ingredient adhered to or distributed through a basic matrix of an inert, finely divided particulate extender. In order to aid leaching of the active ingredient from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the fungicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The method of the present invention may be carried out by mixing the composition comprising the active ingredient into the seed prior to planting at rates from 0.01 to 50 g per kg of seed, preferably from 0.1 to 5 g per kg, and more preferably from 0.2 to 2 g per kg. If application to the soil is desired, the compounds may be applied at rates from 10 to 1000 g per hectare, preferably from 50 to 500 g per hectare. The higher application rates will be needed for situations of light soils or greater rainfall or both.

The compounds useful in the present invention may be prepared by methods known to those of ordinary skill in the art. The following examples illustrate some of these methods and are illustrative only; they are not meant to be limiting in any way.

Unless otherwise indicated, percentages are given as weight/weight. Melting points and boiling points are reported uncorrected. Thin layer chromatography was carried out with varying concentrations of ethyl acetate/hexanes elutions. Tetrahydrofuran and ether solvents were distilled from sodium metal/benzophenone immediately prior to use. N,N,N,N'-(Tetramethyl)ethylenediamine was distilled from calcium hydride prior to use. All other reagents were purchased from Aldrich or Lancaster and used without purification. A measured physical property is reported for each example.

The following abbreviations have the meanings shown:

| | |
|---|---|
| n-BuLi | n-Butyl lithium |
| s-BuLi | sec-Butyl lithium |
| t-BuLi | tert-Butyl lithium |
| DMF | Dimethylformamide |
| DMSO | Dimethylsulfoxide |
| THF | Tetrahydrofuran |
| TMEDA | N,N,N,,N,-(tetramethyl) ethylenediamine |
| eq | equivalent(s) |
| aq | aqueous |
| sat | saturated |
| min. | minutes |
| h | hours |
| MeI | Methyl iodide |
| TLC | Thin Layer Chromatography |
| HPLC | High Pressure Liquid Chromatography |
| RC | Radial Chromatography |
| GLC | Gas-liquid Chromatography |
| RT | room temperature |
| m.p. | melting point |

General Methods

Generally, the process of the present invention is as set out in either of the following Schemes.

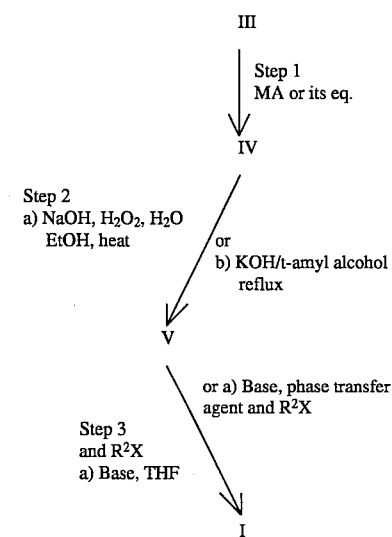

I, III, IV, and V represent compounds of the formula as defined in the corresponding description of the process above, including the limitation in this SCHEME I that I is as defined above but wherein A is defined as $OR^6$ and $R^6$, as well as MA, and $R^2$ is as defined above.

A preferred embodiment of the process shown as Scheme I of the present invention is a one-pot process including step 1, step 2 and step 3 which may provide about a 61% yield.

Another preferred embodiment of the process shown as Scheme I of the present invention is a one-pot process including step 1 and step 2.

Another preferred embodiment of the process Shown as Scheme I of the present invention is a one-pot process including step 2 and step 3.

SCHEME II

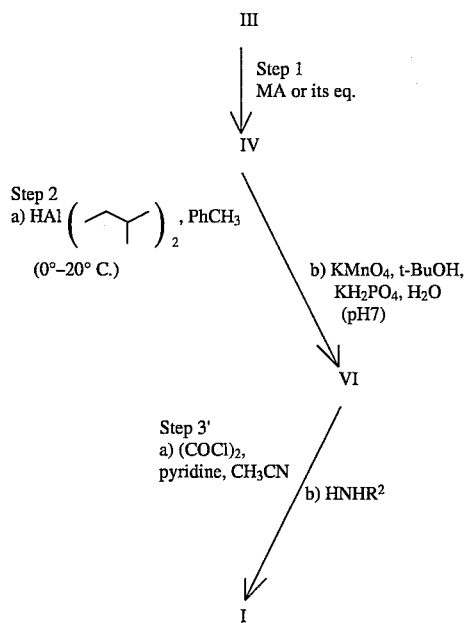

I, III, IV, and VI represent compounds of the formula as defined in the corresponding description of the process above, including the limitation in this SCHEME II that I is as defined above wherein A is defined as $OR^6$ and $R^6$, as well as MA, and $H_2NR^2$ wherein $R_2$ is as defined above.

The process of Step 1 in both Schemes I and II may be carried out in a solvent such as THF, dioxane, DMF, DMSO, AH,1,2-dimethoxyethane, or other polar aprotic solvents.

Starting Materials 2-fluoro-5,6-dichlorobenzaldehyde

A solution of 1.3M s-butyl lithium in cyclohexane (244 mL, 317 mmol) is added to a dry-ice/acetone cooled solution of TMEDA (34 g, 293 mmol) in THF (250 mL), maintaining the internal reaction temperature <–70° C. The resulting reaction mixture is cooled and maintained at ≦–90° C. with an ether/liquid nitrogen bath while a solution of 1,2-dichloro-4-fluorobenzene (40 g, 244 mmol) in THF (100 mL) is added dropwise. The resulting reaction mixture is stirred with dry-ice/acetone cooling for 1h, then is cannulated into an ether/liquid nitrogen cooled and mechanically stirred solution of DMF (89.1 g, 1.22 mol) in THF (125 mL). The resulting mixture is warmed to –45° C. and partitioned between dilute aqueous HCl and ether. The organic solution is washed with aqueous $NaHCO_3$, dried ($MgSO_4$), and concentrated to afford 44.38 g of 2-fluoro-5,6-dichlorobenzaldehyde as an oil.

2-fluoro-5-methyl-6-chlorobenzaldehyde

A solution of 1.3M s-butyl lithium in cyclohexane (75 mL, 98 mmol) is added to a dry-ice/acetone cooled solution of TMEDA (9.67 g, 83 mmol) in THF (90 mL), maintaining the internal reaction temperature <–70° C. The reaction mixture is cooled and maintained at ≦–80° C. with an ether/liquid nitrogen bath while a solution of 2-chloro-4-fluorotoluene (10 g, 69 mmol) in THF (10 mL) is added dropwise. The resulting reaction mixture is stirred with dry-ice/acetone cooling for 1h, then is cannulated into an ether/liquid nitrogen cooled and mechanically stirred solution of DMF (25.1 g, 345 mmol) in THF (50 mL). The resulting mixture is warmed to –30° C. and partitioned between dilute aqueous HCl and ether. The organic solution is washed with aqueous $NaHCO_3$, dried ($MgSO_4$), and concentrated and triturated with hexanes to afford 2-fluoro-5-methyl-6-chlorobenzaldehyde as a crystalline solid.

2-fluoro-5-methyl-6-chlorobenzonitrile

Hydroxylamine hydrochloride (1.1 parts) is added to a solution of 2-fluoro-5-methyl-6-chlorobenzaldehyde in pyridine, and the mixture is stirred for 15 minutes at room temperature. Acetic anhydride (1.3 parts) is then added and the mixture stirred at ambient temperature overnight to effect complete dehydration of the oxime to the nitrile. Most of the pyridine is removed by concentration under vacuum, then the residue is partitioned between ether and water. The organic phase is washed with brine, dried (MgSO4), filtered through silica gel, concentrated, then triturated in hexane to afford 2-fluoro-5-methyl-6-chlorobenzonitrile as light yellow crystals.

Method A $NaN_3$ (2 parts) is carefully added to a 1.5M solution of the optionally 5-substituted- 2-chloro-6-fluorobenzaldehyde (1 part) in DMSO, and the mixture is slowly heated to 75° C. for 2h. The reaction temperature is then raised to 100° C. and the formation of the anthranil is monitored to completion over about 3h by $^1$H-NMR analysis of the aromatic region. The dark solution is partitioned between water and ether, then filtered through celite to break up the emulsion. The aqueous is extracted with additional ether, then the combined organic extracts are washed with water, dried ($MgSO_4$), concentrated, and kugelrohr distilled to afford the anthranils as light yellow solids in yields ranging from 40–85%.

A mixture of one of these anthranils (1 part) and a tert-alkanol (1.1 to 1.2 parts) is warmed to effect solution, then is cooled in an ice-water bath while 70% perchloric acid or 60% hexafluorophosphoric acid (2 parts) is added at a rate which maintained the internal reaction temperature ≦35° C. After addition, the reaction mixture is stirred with ice-water cooling while the precipitate formed over about 30 minutes. This is slurried in ether and the salts are collected by filtration, washed with dry ether, and dried under vacuum to give the N-tert-alkyl anthranilium perchlorate or hexafluorophosphate salt as pale yellow solids in high yields.

This N-tert-alkyl anthranilium salt (1 part) is added in portions to an ice-water cooled 1.5M solution of $Et_3N$ (3 parts) in $CH_2Cl_2$. The resulting amber solution is stirred at room temperature for 30 min, then is concentrated to a small volume, diluted with dry ether, and filtered to remove the salts. This solution is concentrated to an oil, then is dissolved in hexanes and decanted to remove the insoluble material.

Concentration of the hexane solution gave the desired β-lactam as a golden oil in high yield.

Method B

The β-lactam from Method A (1 part), optionally dissolved in a small volume of an organic solvent, is added dropwise to an ice-water cooled solution of a primary amine (5 to 10 parts) in $CH_2Cl_2$. The resulting mixture is stirred 0.5–1.0 hour, then is either concentrated and recrystallized from hexanes or partitioned between water and an organic solvent. From the extractive workup, the organic solution is dried ($MgSO_4$), concentrated, slurried in hexanes, then filtered to give the N-alkyl 2-tert-alkylamino benzamide as a solid.

Method C

The β-lactam from Method A (1 part) is refluxed in methanol (35 parts) for 1 hour, then is concentrated to afford the methyl ester as an oil. An 0.2M solution of this methyl ester in DMF is combined with potassium carbonate (2 parts) and methyl iodide (5 parts) then heated overnight at 80° C. in a sealed tube. This is diluted with ether, washed with water, dried ($MgSO_4$) and concentrated to afford the N-methylated ester as a dark oil.

An alkylamine (1.5 parts) is added to butyl lithium in hexanes (1 part) at –78 C to afford a hexane solution of the N-lithio alkylamine. A solution of this N-lithio alkylamine (6 parts) is added to a –78° C. cooled 1M solution of the N-methylated ester from above (1 part) in THF. The resulting reaction mixture is maintained at 0° C. overnight, then is diluted with ether, washed with water, dried ($MgSO_4$), concentrated, and purified by chromatography to afford the desired N-alkylated benzamide as a solid.

Method D

An 80% oil dispersion of sodium hydride (1.2 parts) is added to a solution of 2-chloro-6-fluorobenzonitrile (1 part) and a tert-alkanol (1.2 parts) dissolved in dry 1,4-dioxane. The mixture is refluxed for 16–20 hours, then is partitioned between ether and water. The organic layer is washed with brine, dried (MgSO4), then is filtered through silica gel and concentrated. This crude 2-tert-alkoxy-6-chlorobenzonitrile is dissolved in t-amyl alcohol and enough potassium hydroxide pellets are added to maintain saturation at reflux. The mixture is refluxed for 2 hours, then is concentrated under vacuum and the residue is partitioned between ether and water. The organic layer is washed with brine, dried (MgSO4) and filtered through silica gel. Then the filtrate is concentrated and the residue triturated with hexane to give the desired 2-alkoxy-6-chlorobenzamide which is recrystallized from hexanes.

Method E

A 35% oil dispersion of potassium hydride (1 part) is added to a solution of a tert-alkanol in dry 1,2-dimethoxyethane. This mixture is briefly refluxed to achieve complete formation of the potassium alkoxide, then is cooled to room temperature and 0.9 part of either 2-chloro-6-fluorobenzonitrile or 2-chloro-3-methyl-6-fluorobenzonitrile is added. The resulting mixture is stirred for 20 minutes, then is partitioned between ether and water. The organic layer is washed with brine, dried (MgSO4), and is filtered through silica gel and concentrated. The residue is passed through a 4 inch plug of silica gel by eluting first with hexanes to remove the mineral oil then with 1:3 ethyl acetate/hexanes to give the desired benzonitrile. This purified 2-tert-alkoxy benzonitrile is dissolved in tert-amyl alcohol and enough potassium hydroxide pellets are added to maintain saturation at reflux. The mixture is refluxed for 2 hours, then is concentrated under vacuum and the residue is partitioned between ether and water. The organic layer is washed with brine, dried (MgSO4) and filtered through silica gel. Then the filtrate is concentrated and the residue triturated with hexane to give either the 2-tert-alkoxy-6-chlorobenzamide or the 2-tert-alkoxy-5-methyl-6-chlorobenzamide which is recrystallized from hexanes.

Method F

N-Chlorosuccinimide (2.4 parts) is added to a solution of the primary benzamide (from method D or E) in dry acetonitrile, and the mixture is refluxed for 1 hour. This is partitioned between ether and aqueous $Na_2S_2O_3$ and the organic layer is washed with 10% NaOH followed with brine, dried (MgSO4), filtered through silica gel, and concentrated to give the crude 5-chlorobenzamide.

Method G

To a solution of the primary benzamide from method D, E, or F (1 part) in dry THF is added solid lithium bis(trimethylsilyl)amide (1.1 part) or a 1.0M solution of sodium bis(trimethylsilyl)amide in THF (1.2 parts). After stirring this mixture for 5 min, the appropriate alkyl halide (2 parts) is added and the reaction is refluxed for 3 hours. This is partitioned between ether and water, and the organic layer is washed with brine, dried (MgSO4), filtered through silica gel, and concentrated to give the crude N-alkyl benzamide which is purified by recrystallization or chromatography.

Method H

To a solution of the primary benzamide from method D, E, or F (1 part) and a phase transfer catalyst, tetrabutylammonium hydrogen sulfate (0.02 part), in toluene is added an equal volume of 50% NaOH and the appropriate alkyl halide (2.2 parts), and the mixture is refluxed for 45 min. This is partitioned between ether and water, and the organic layer is washed with brine, dried (MgSO4), filtered through silica gel, and concentrated to give the crude N-alkyl benzamide which is purified by recrystallization or chromatography.

The following compounds are prepared using Methods A and B.

TABLE 1

| EX.NO. | COMPOUND | M.P. |
|---|---|---|
| 1 | N-allyl 2-[(1,1-dimethyl ethyl)amino]-6-chlorobenzamide | 107–108° C. |
| 2 | N-propyl 2-[(1,1-dimethyl ethyl)amino]-6-chlorobenzamide | 112–113° C. |
| 3 | N-ethyl 2-[(1,1-dimethyl propyl)amino]-6-chlorobenzamide | 93–95° C. |
| 4 | N-propyl 2-[(1,1-dimethyl propyl)amino]-6-chlorobenzamide | 99–101° C. |
| 5 | N-ethyl 2-[(1,1-diethyl ethyl)amino]-6-chlorobenzamide | 105–106° C. |
| 6 | N-allyl 2-[(1,1-diethyl ethyl)amino]-6-chlorobenzamide | 77–79° C. |
| 7 | N-propyl 2-[(1,1-diethyl ethyl)amino]-6-chlorobenzamide | 74–75° C. |
| 9 | N-allyl 2-[(1,1-diethyl | 105–107° C. |

TABLE 1-continued

| EX.NO. | COMPOUND | M.P. |
|---|---|---|
|  | propyl)amino]-6-chlorobenzamide |  |
| 10 | N-propyl 2-[(1,1-diethyl propyl)amino]-6-chlorobenzamide | 99–100° C. |
| 11 | N-ethyl 2-[(1-methyl-1-cyclopentyl)amino]-6-chlorobenzamide | 116–117° C. |
| 12 | N-allyl 2-[(1-methyl-1-cyclopentyl)amino]-6-chlorobenzamide | 100–102° C. |
| 13 | N-propyl 2-[(1-methyl-1-cyclopentyl)amino]-6-chlorobenzamide | 126–128° C. |
| 15 | N-allyl 2-[(1-methyl-1-cyclohexyl)amino]-6-chlorobenzamide | 110–111° C. |
| 16 | N-ethyl 2-[(1,1-dimethyl ethyl)amino]-5-methyl-6-chlorobenzamide | 131–133° C. |
| 17 | N-allyl 2-[(1,1-dimethyl ethyl)amino]-5-methyl-6-chlorobenzamide | 128–130° C. |
| 18 | N-propyl 2-[(1,1-dimethyl ethyl)amino]-5-methyl-6-chlorobenzamide | 131–132° C. |
| 19 | N-ethyl 2-[(1,1-dimethyl propyl)amino]-5-methyl-6-chlorobenzamide | 106–108° C. |
| 20 | N-allyl 2-[(1,1-dimethyl propyl)amino]-5-methyl-6-chlorobenzamide | 89–92° C. |
| 21 | N-propyl 2-[(1,1-dimethyl propyl)amino]-5-methyl-6-chlorobenzamide | 98–100° C. |
| 22 | N-ethyl 2-[(1,1-diethyl ethyl)amino]-5-methyl-6-chlorobenzamide | 109–110° C. |
| 23 | N-allyl 2-[(1,1-diethyl ethyl)amino]-5-methyl-6-chlorobenzamide | 101–102° C. |
| 24 | N-ethyl 2-[(1,1-diethyl propyl)amino]-5-methyl-6-chlorobenzamide | 104–107° C. |
| 25 | N-allyl 2-[(1,1-diethyl propyl)amino]-5-methyl-6-chlorobenzamide | 84–88° C. |
| 26 | N-propyl 2-[(1,1-diethyl propyl)amino]-5-methyl-6-chlorobenzamide | 89–92° C. |
| 27 | N-allyl 2-[(1,1-dimethyl ethyl)amino]-5,6-dichlorobenzamide | 125–126° C. |
| 28 | N-propyl 2-[(1,1-dimethyl ethyl)amino]-5,6-dichlorobenzamide | 146–148° C. |
| 29 | N-ethyl 2-[(1,1-dimethyl propyl)amino]-5,6-dichlorobenzamide | 128–130° C. |
| 30 | N-allyl 2-[(1,1-dimethyl propyl)amino]-5,6-dichlorobenzamide | 97–98° C. |
| 31 | N-propyl 2-[(1,1-dimethyl propyl)amino]-5,6-dichlorobenzamide | 102–104° C. |
| 32 | N-ethyl 2-[(1,1-diethyl ethyl)amino]-5,6-dichlorobenzamide | 106–108° C. |
| 33 | N-allyl 2-[(1,1-diethyl ethyl)amino]-5,6-dichlorobenzamide | 100–102° C. |
| 34 | N-propyl 2-[(1,1-diethyl ethyl)amino]-5,6-dichlorobenzamide | 81–83° C. |
| 35 | N-ethyl 2-[(1,1-diethyl propyl)amino]-5,6-dichlorobenzamide | 123–125° C. |
| 36 | N-allyl 2-[(1,1-diethyl propyl)amino]-5,6-dichlorobenzamide | 83–86° C. |
| 37 | N-propyl 2-[(1,1-diethyl propyl)amino]-5,6-dichlorobenzamide | 88–90° C. |
| 38 | N-ethyl 2-[(1-methyl-1-cyclopentyl)amino]-5,6-dichlorobenzamide | 135–136° C. |
| 39 | N-allyl 2-[(1-methyl-1-cyclopentyl)amino]-5,6-dichlorobenzamide | 106–109° C. |
| 40 | N-propyl 2-[(1-methyl-1-cyclopentyl)amino]-5,6-dichlorobenzamide | 122–125° C. |

The following compounds were made using Methods A and C.

TABLE 2

| EX.NO. | COMPOUND | M.P. |
|---|---|---|
| 41 | N-ethyl 2-[N-methyl-N-(1,1-dimethyl ethyl)amino]-5-methyl-6-chlorobenzamide | 111–114° C. |
| 42 | N-propyl 2-[N-methyl-N-(1,1-dimethyl ethyl)amino]-5-methyl-6-chlorobenzamide | 129–131° C. |
| 43 | N-ethyl 2-[N-methyl-N-(1,1-dimethyl propyl)amino]-5-methyl-6-chlorobenzamide | 122–125° C. |

The following compounds were made using Method G or H.

TABLE 3

| EX.NO. | COMPOUND | METHOD | M.P. |
|---|---|---|---|
| 45 | N-allyl 2-[(1,1-dimethyl propyl)oxy]-6-chlorobenzamide | G | 93–94° C. |
| 46 | N-propyl 2-[(1,1-dimethyl propyl)oxy]-6-chlorobenzamide | G | 99–100° C. |
| 47 | N-ethyl 2-[(1,1-diethyl ethyl)oxy]-6-chlorobenzamide | G | 96–98° C. |
| 48 | N-allyl 2-[(1,1-diethyl ethyl)oxy]-6-chlorobenzamide | G | 87–88° C. |
| 49 | N-propyl 2-[(1,1-diethyl ethyl)oxy]-6-chlorobenzamide | H | 100–102° C. |
| 52 | N-allyl 2-[(1,1,2-trimethyl propyl)oxy]-6-chlorobenzamide | G | 102–103° C. |
| 55 | N-allyl 2-[(1,1,2,2-tetramethyl propyl)oxy]-6-chlorobenzamide | G | 115–116° C. |
| 56 | N-isopropyl 2-[(1,1-diethyl ethyl)oxy]-6-chlorobenzamide | G | 107–108° C. |
| 59 | N-allyl 2-[(1,1-diethyl propyl)oxy]-6-chlorobenzamide | G | 87–88° C. |
| 60 | N-propyl 2-[(1,1-diethyl propyl)oxy]-6-chlorobenzamide | G | 94–96° C. |
| 63 | N-allyl 2-[(1-methyl-1-cyclopentyl)oxy]-6-chlorobenzamide | G | 86–87° C. |
| 66 | N-allyl 2-[(1-methyl-1- | G | 94–96° C. |

TABLE 3-continued

| EX.NO. | COMPOUND | METHOD | M.P. |
|---|---|---|---|
|  | cyclohexyl)oxy]-6-chlorobenzamide |  |  |
| 67 | N-propyl 2-[(1-methyl-1-cyclohexyl)oxy]-6-chlorobenzamide | G | 95–96° C. |
| 68 | N-allyl 2-[(1,1-diethylethyl)oxy]-5,6-dichlorobenzamide | H | 117–118° C. |
| 69 | N-propyl 2-[(1,1-diethylethyl)oxy]-5,6-dichlorobenzamide | H | 103–104° C. |
| 70 | N-propyl 2-[(1-methyl-1-cyclohexyl)oxy]-5,6-dichlorobenzamide | H | 129–130° C. |
| 71 | N-allyl 2-[(1,1-diethylethyl)oxy]-5-methyl-6-chlorobenzamide | H | 80–81° C. |
| 72 | N-propyl 2-[(1,1-diethylethyl)oxy]-5-methyl-6-chlorobenzamide | H | 85–86° C. |
| 73 | N-ethyl-2-[(1,1,2-trimethylpropyl)amino]-6-chlorobenzamide | A B | 90–93° C. |

The processes useful in the present invention may include variations within the ordinary skill in the art. The following examples illustrate some of the specific methods of the processes and are illustrative only; they are not meant to be limiting in any way.

EXAMPLE OF SCHEME II

To a solution of 2-fluoro-6-chlorobenzonitrile (10.35 g, 66.5 mmol) in 1,2-dimethoxyethane (50 mL) at 0° C. was added potassium t-butoxide (9.06 g, 80.7 mmol). The mixture was slowly allowed to warm to room temperature over 3 h. The reaction was poured into water and extracted with ether (3 times). The organic layers were washed with brine, dried (MgSO$_4$) and concentrated to afford 13.52 g (97%) of 2-[(1,1-dimethylethyl)oxy]-6-chlorobenzonitrile as a pale yellow oil.

To a solution of 2-[(1,1-dimethylethyl)oxy]-6-chlorobenzonitrile (9.22 g, 44.0 mmol) in toluene (100 mL) cooled in an ice-bath was added diisobutylaluminum hydride (1M in hexane, 48.4 mL, 48.4 mmol) keeping the temperature less than 10° C. The reaction was stirred for 1 h and was poured into a mixture of 10% aqueous acetic acid (100 mL) and ice. The mixture was filtered through Celite, the layers separated and the aqueous layer extracted with ether (2 times). The combined organic layers were washed with saturated sodium bicarbonate, brine, dried (MgSO$_4$) and concentrated to afford 9.07 g (97%) of 2-[(1,1-dimethylethyl)oxy]-6-chlorobenzaldehyde as a yellow oil.

To a solution of 2-[(1,1-dimethylethyl)oxy]-6-chlorobenzaldehyde (8.40 g, 40.0 mmol) in t-butanol (200 mL) was added 1.25M KH$_2$PO$_4$ (pH 7, 200 mL) and 0.4M aqueous potassium permanganate (200 mL, 80 mmol). The reaction was stirred at room temperature for 3 h and was quenched by the addition of saturated aqueous sodium sulfite (200 mL). The brown suspension was acidified with 2N HCl with ice-cooling until the MnO$_2$ dissolved (pH 4). The reaction was extracted with ethyl acetate (3 times) and the organic layers were washed with brine, dried (MgSO$_4$) and concentrated to a white solid. The crude product was recrystallized from hexanes at 0° C. to afford 7.14 g (78%) of 2-[(1,1-dimethylethyl)oxy]-6-chlorobenzoic acid as white crystals: mp 117°–119° C.

2-[(1,1-dimethylethyl)oxy]-6-chlorobenzoic acid (68.6 mg, 0.3 mmol) was weighed into a 1 dram septum-capped vial containing a micro stir bar under nitrogen. Dry acetonitrile (300 microliter), dry pyridine (24 microliter, 0.3 mmol) and oxalyl chloride (26 microliter, 0.3 mmol) were added in order to the vial using microliter syringes. The yellow homogeneous solution was stirred for 30 minutes to afford a solution of 2-[(1,1-dimethylethyl)oxy]-6-chlorobenzoyl chloride.

Ethyl amine hydrochloride (16.3 mg, 0.20 mmol) was weighed into a 1 dram vial containing a microstirbar. Water (100 microliter), acetonitrile (300 microliter) and triethylamine (200 microliter) were added in the specified order to the vial using microliter syringes. This afforded a clear and colorless solution which was charged with the solution of 2-[(1,1-dimethylethyl)oxy]-6-chlorobenzoyl chloride (0.30 mmol). The yellowish reaction was stirred for 30 minutes.

Glutathione (50 mg, 0.16 mmol) was then added and the reaction was stirred for an additional 30 minutes. Diethyl ether (1.5 mL) was added and the mixture extracted with water (1 mL), 2.5N NaOH (1 mL) and brine (1 mL) to remove all of the byproducts. This was accomplished by vigorously stirring the reaction mixture with each wash for a few minutes, followed by the removal of the wash with a 500 microliter syringe. The ether was dried over sodium sulfate, filtered through a disposable pipette containing a piece of AccuWipe as filter and concentrated to afford 44 mg of pure N-ethyl 2-[(1,1-dimethylethyl)oxy]-6-chlorobenzamide as a white crystalline solid in 86% yield.

Example of Step 3 of SCHEME I—Phase-Transfer Monoalkylation—preparation of Example No. 49 above.

A mixture of 2-[(1,1-diethylethyl)oxy]-6-chlorobenzamide (1.00 g, 3.9 mmol) and tetrabutylammonium bisulfate (0.13 g, 0.4 mmol) in 50% aqueous sodium hydroxide (25 mL) and toluene (15 mL) was heated to 100° C. and n-propyl bromide (0.43 mL, 4.7 mmol) in toluene (10 mL) was added over 30 min. The reaction was heated for 1 h, was cooled and poured into water. The mixture was extracted with ether and the organic layers were washed with brine, dried (MgSO$_4$) and concentrated to a white solid. The crude product was purified by radial chromatography to afford 0.78 g (67%) of N-propyl 2-[(1,1-diethylethyl)oxy]-6-chlorobenzamide as a white solid: mp 100°–102° C.

Example of an Analogous One Pot Practice of Scheme I

To a slurry of potassium t-butoxide (56.0 g, 0.5 mol) in t-butanol (200 mL) at room temperature was added 2-fluorobenzonitrile (12.1 g, 0.1 mol). The reaction mixture was heated to reflux for 30 min and water (3.6 mL, 0.2 mol) was added. The reaction was heated at reflux for 2 h and ethyl iodide (40 mL, 0.5 mol) was added portionwise over 40 min as reflux was continued. After cooling and stirring at room temperature overnight, GC and GC MS analysis of the reaction indicated a 61% yield of N-ethyl 2-[(1,1-dimethylethyl)oxy]benzamide. Thus, using appropriate analogous conditions the compounds of this invention can be made in a one pot process.

One Pot for Scheme I Step 1 and Step 2(b)
Benzamide, 2-Chloro-6-(1-Ethyl-1-Methylpropoxy)-.

To 100 g (980 mmol) of 3-methyl-3-pentanol heated to 120° C. was added in small portions 15.0 g (385 mmol) of potassium. when all of the potassium had dissolved, the mixture was allowed to cool to 65° C. and to the mixture was added a solution of 50.0 g (322 mmol) of 2-chloro-6-fluorobenzonitrile in 100 ml of toluene. The mixture was cooled on an ice bath during addition and addition took 10 minutes. Stirring at ambient was continued for another 15 minutes and the mixture was then heated to 90° C. At this point none of the starting material remained. To the mixture was added 50 g of potassium hydroxide pellets and 200 ml of t-amyl alcohol. The mixture was heated to reflux for 45 minutes and was allowed to cool to room temperature overnight. Solvent was removed in vacuo and the residue was partitioned between ether and water. The organic layer was washed with brine, dried (MgSO$_4$), and was filtered through silica gel. The filtrate was evaporated in vacuo and the residue was recrystallized from hexane to yield 70.0 g (85%) of white crystals.

BIOLOGICAL ASSAYS

The compounds prepared in the above examples have demonstrated control of Ggt in one or both of the following test methods. The results are shown in the tables below.

In vitro Assay

The test compounds (0.25 mL of an appropriate stock solution in acetone) are incorporated into 25 mL minimal media agar [prepared by autoclaving a solution of 17.5 g Czapek Dox broth (Difco), 7.5 g purified agar or Bacto-agar (Difco), and 500 mL distilled/deionized water, and then adding 50 μL of 1 mg/mL thiamine hydrochloride and 50 μL of 1 mg/mL biotin in 5% ethanol] and plates are prepared.

Each plate is inoculated by placing in a triangular shape three 4-mm plugs of *Gaeumannomyces graminis* var. tritici (Ggt) grown on the minimal media agar described above. The plates are incubated in the dark at 19°–20° C. for 4 to 5 days. The growth of the fungus is measured as the diameter of the mycelial growth. The result is expressed as Percent Inhibition, calculated as [1- [(mm growth on treated plate - 4)/(mm growth on control plate - 4)]] x 100.

Seed/Soil Drench In vivo Assay

Compounds are tested for control of Ggt on 'Bergen' or 'Anza' varieties of wheat grown in 3-inch square pots containing soil infested with Ggt. The infestation is accomplished by mixing the soil with an inoculum prepared by growing Ggt on ¼ strength potato dextrose agar (4.875 g potato dextrose agar, 5.0 g Bacto agar, 500 mL distilled, deionized water) in plates and using plugs from the plates to infest sterile oats (400 cc whole oats, 350 mL deionized water, autoclaved). After a one-month incubation period at room temperature, the oats are dried and mixed with the soil at 4% v/v. Four wheat seeds are placed on top of the soil in each pot. The test compounds are prepared as an 1:9 acetone/water v/v solution containing 0.18% Tween® 20 to provide a treatment rate of 0.5 and/or 0.1 mg active ingredient per pot, treated with 3 mL test solution per pot. Five pots are used for each treatment level and the controls, which are untreated, inoculated and non-inoculated pots. After one hour drying time, the seeds are covered with more of the appropriate soil and a layer of vermiculite. The pots are placed in a growth chamber and watered each day. After four weeks, each pot is evaluated for evidence of disease by examination of the seminal roots of each plant under a dissecting microscope. A 0 to 5 rating scale having the following meanings is used:

0=no runner hyphae or lesions present

1=runner hyphae and a few small lesions present on <10% of root system

2=runner hyphae and small lesions present on 10–25% of root system

3=runner hyphae and lesions present on 25–50% of root system

4=runner hyphae and many, large, coalescing lesions on >50% of root system

5=root system and culm completely inundated with lesions and runner hyphae

From each set of five replicates a high or low score may be eliminated to assure the best representative scores are used to calculate a replicate mean by averaging the remaining scores. This mean score is then compared to the untreated control score and a percent disease control is calculated.

The results of these in vitro and in vivo tests are reported in the Table below. If the calculation resulted in "0" or less, as compared to the untreated control, a "N" is shown to indicate no control.

| | In Vitro (ppm) | | | In Vivo mg/pot | | |
|---|---|---|---|---|---|---|
| EX.NO. | 10 | 1.0 | 0.1 | 0.5 | 0.1 | 0.02 |
| 5 | 95 | 95 | 93 | 92 | 93 | 65 |
| 3 | 97 | 97 | 97 | 100 | 97 | 60 |
| 73 | 94 | 94 | 94 | 96 | 62 | 16 |
| 16 | 100 | 98 | 98 | 100 | 99 | 73 |
| 17 | 98 | 98 | 98 | 97 | 99 | 97 |
| 19 | 100 | 98 | 98 | 100 | 97 | 97 |
| 20 | 100 | 98 | 98 | 100 | 100 | 97 |
| 22 | 97 | 97 | 97 | 99 | 95 | 88 |
| 23 | 97 | 97 | 97 | 89 | 79 | 53 |
| 41 | 98 | 98 | 90 | 99 | 64 | 44 |
| 42 | 98 | 98 | 93 | 100 | 96 | 72 |
| 21 | 100 | 97 | 97 | 100 | 99 | 97 |
| 10 | 56 | 46 | 56 | | No Data* | |
| 17 | 97 | 95 | 95 | 99 | 91 | 59 |
| 4 | 100 | 97 | 97 | 100 | 100 | 84 |
| 43 | 98 | 98 | 98 | 100 | 100 | 64 |
| 18 | 98 | 98 | 98 | 100 | 100 | 70 |
| 11 | 81 | 85 | 81 | 100 | 97 | 31 |
| 46 | 96 | 96 | 96 | 99 | 97 | 77 |
| 49 | 96 | 91 | 96 | 100 | 89 | 96 |
| 47 | 100 | 97 | 97 | 100 | 100 | 93 |
| 56 | 100 | 97 | 97 | 100 | 100 | 90 |
| 63 | 100 | 97 | 97 | 100 | 77 | 40 |
| 55 | 100 | 100 | 97 | 99 | 89 | 68 |
| 1 | 100 | 97 | 100 | 96 | 100 | 90 |
| 6 | 100 | 100 | 100 | 100 | 100 | 77 |
| 15 | 100 | 100 | 97 | 100 | 100 | 93 |
| 9 | 100 | 100 | 97 | 97 | 99 | 94 |
| 2 | 100 | 100 | 100 | 100 | 99 | 92 |
| 66 | 98 | 95 | 95 | 100 | 100 | 90 |
| 48 | 100 | 100 | 98 | 100 | 100 | 85 |
| 59 | 95 | 95 | 88 | 99 | 92 | 80 |
| 52 | 98 | 98 | 95 | 100 | 99 | 55 |
| 45 | 98 | 98 | 95 | 100 | 99 | 81 |
| 67 | 97 | 97 | 95 | 100 | 87 | 64 |
| 60 | 95 | 88 | 81 | 100 | 76 | 49 |
| 71 | 98 | 98 | 98 | 96 | 89 | 70 |
| 72 | 98 | 98 | 98 | 100 | 96 | 85 |
| 70 | 98 | 95 | 72 | 81 | 47 | 19 |
| 24 | 97 | 97 | 97 | 45 | 41 | 19 |
| 26 | 97 | 97 | 97 | 60 | 47 | 27 |
| 25 | 100 | 97 | 97 | 85 | 63 | 35 |
| 13 | 97 | 97 | 97 | 85 | 87 | 55 |
| 12 | 100 | 97 | 97 | 99 | 77 | 72 |
| 29 | 100 | 98 | 98 | 80 | 67 | 36 |
| 31 | 98 | 98 | 98 | 84 | 73 | 40 |
| 30 | 100 | 98 | 98 | 93 | 67 | 55 |
| 32 | 98 | 98 | 95 | 53 | 44 | 41 |

-continued

| EX.NO. | In Vitro (ppm) | | | In Vivo mg/pot | | |
|---|---|---|---|---|---|---|
| | 10 | 1.0 | 0.1 | 0.5 | 0.1 | 0.02 |
| 34 | 98 | 95 | 93 | 57 | 41 | 37 |
| 33 | 98 | 98 | 98 | 52 | 43 | 40 |
| 27 | 98 | 98 | 95 | 80 | 75 | 45 |
| 28 | 98 | 98 | 90 | 92 | 80 | 41 |
| 38 | 100 | 98 | 93 | 52 | 41 | 21 |
| 35 | 93 | 88 | 83 | 31 | 45 | 15 |
| 36 | 98 | 98 | 98 | 55 | 43 | 25 |
| 39 | 98 | 98 | 98 | 51 | 53 | 36 |
| 40 | 98 | 98 | 98 | 37 | 47 | 32 |
| 37 | 88 | 85 | 83 | 41 | 33 | 27 |
| 68 | 100 | 95 | 98 | 94 | 86 | 61 |
| 69 | 98 | 98 | 84 | 93 | 89 | 50 |

*This compound did not show enough in vitro activity to warrant a secondary test.

To determine $IC_{50}$ values, an in vitro assay was run on each compound at the concentrations of 1, 0.1, 0.01, 0.001, and 0.0001 ppm. The percent inhibition was calculated for each concentration using the equation described in the in vitro assay under the section on Biological Assays. Using the two ordered pairs of (concentration, % inhibition) that bracket 50% inhibition of fungal growth, the concentration for 50% inhibition is calculated from the following equation. $IC_{50}=[(50-I_2)C_1+(I_1-50)C_2]/(I_1-I_2)$, where $C_1=10C_2$. Results of In vitro Assay.

TABLE 4

| IC50 VALUES | |
|---|---|
| EX.NO. | IC50 |
| Std.[1] | 0.029636 |
| Std.[2] | 0.056154 |
| 23 | 0.000100 |
| 21 | 0.000100 |
| 25 | 0.000100 |
| 26 | 0.000200 |
| 20 | 0.000421 |
| 6 | 0.000629 |
| 2 | 0.000629 |
| 9 | 0.000654 |
| 24 | 0.000700 |
| 19 | 0.000728 |
| 22 | 0.000762 |
| 17 | 0.000779 |
| 4 | 0.000850 |
| 15 | 0.001000 |
| 18 | 0.001383 |
| 7 | 0.003700 |
| 3 | 0.005598 |
| 5 | 0.005932 |
| 1 | 0.006000 |
| 16 | 0.006143 |
| 73 | 0.006548 |
| 11 | 0.006625 |
| 42 | 0.006769 |
| 41 | 0.008500 |
| 43 | 0.008500 |
| Std.[1] | 0.045410 |
| Std.[2] | 0.031522 |
| 36 | 0.000616 |
| 31 | 0.000640 |
| 33 | 0.000661 |
| 12 | 0.000706 |
| 13 | 0.000728 |
| 39 | 0.000759 |
| 30 | 0.000765 |
| 34 | 0.000765 |
| 40 | 0.002620 |
| 32 | 0.006164 |
| 28 | 0.006239 |

TABLE 4-continued

| IC50 VALUES | |
|---|---|
| EX.NO. | IC50 |
| 37 | 0.006571 |
| 38 | 0.006750 |
| 29 | 0.006754 |
| 27 | 0.007362 |
| 35 | 0.007571 |
| Std.[1] | 0.044500 |
| Std.[2] | 0.094130 |
| 48 | 0.000936 |
| 59 | 0.004900 |
| 63 | 0.005500 |
| 52 | 0.005781 |
| 66 | 0.005944 |
| 49 | 0.006197 |
| 47 | 0.007179 |
| 46 | 0.007242 |
| 56 | 0.008393 |
| Std.[1] | 0.052500 |
| Std.[2] | 0.075323 |
| 71 | 0.000745 |
| 72 | 0.002412 |
| 45 | 0.005792 |
| 67 | 0.006230 |
| 55 | 0.007923 |
| 60 | 0.034894 |

Seed Treatment In vivo Assay

Compounds are tested for control of Ggt on 'Bergen' or 'Anza' varieties of wheat grown in 6-inch round pots containing soil (equal to thirds of Metro-mix, sand, and silt-loam field soil, all steam sterilized). Seeds are treated with a solution of compound of the present invention at 10,000 ppm stock solution in acetone. 20 mg in 2 ml will treat 10 g of seed at each of 4 rates. Using a 10,000 ppm stock for each compound make the following dilutions series:

| | gai/100 kg composition | |
|---|---|---|
| 1 | 100 | 1 ml of stock |
| 2 | 50 | 1 ml stock + 1 ml acetone |
| 3 | 25 | 1 ml #2 + 1 ml acetone |
| 4 | 12.5 | 1 ml #3 + 1 ml acetone (discard 1 ml or proceed) |
| 5 | 6.25 | 1 ml #4 + 1 ml acetone (discard 1 ml) |

(5 is optional and not used in all tests)
*each vial of solution should contain 1 ml to treat 10 g of seed. 10 g packets of wheat seed (variety 'Bergen'), one for each treatment are prepared.

A treatment jar is rinsed 2 times with 3 ml of actone. Then 1 ml of the solution is swirled to cover the base of the jar. 10 g of seed are added to the jar and capped after which the jar is swirled and shaken until the seeds get a rapid and even coverage. After about 30 seconds the lid is removed as the shaking is continued. After 1 minute the jar is set down to dry. When dry, the seed are poured back into the envelope for either planting in the pots or stored until such planting. The method of planting is as follows:

Large Pot Greenhouse Take-All Assay

The 6-inch pots are packed to their ledge with the above soil mix.
Method:

a) Treated seed is placed on the surface of the soil (packed to ledge) at the rate of 8 seeds per pot with the seeds about 2–3 inches apart. 5 pots (replicates) are planted per treatment.
b) 15 ml of oat inoculum (about 4 g) are measured and sprinkled evenly over the soil surface of each pot.
c) The soil/seed/inoculum is covered with 180 ml of soil mix (same as above). A 150 ml beaker filled to the top edge is about 180 ml.
d) Initially each of the prepared pots is watered lightly several times to wet soil without washing out seeds.
e) In cool winter months the prepared pots are left in the greenhouse at 16°–18° C. with only minimal supplemental light. In warmer months the prepared pots are put in a growth chamber set at 17° C. for 3–4 weeks to establish disease, then placed in a greenhouse until harvest. The wheat is harvested, washed, and the roots are rated after 7–10 weeks.
f) Percentage of diseased root area is assigned values using 1, 5, 10, 20, 30, 40, 50, 60, 80, or 100 %. Each pot of plants gets a single rating. Results of advanced 8-week seed treatment In vivo Assay in soil.

TABLE 5

| EX.NO. | % control of root rot | | | | % disease | |
|---|---|---|---|---|---|---|
| | 1 g/kg | 0.5 | 0.25 | 0.125 | non TRT | test # |
| Std.[1] | 14 | 0 | 0 | 0 | 51 | 2 |
| Std.[1] |  | 46 | 16 | 20 | 50 | 3 |
| Std.[1] | 94 | 76 | 32 | 24 | 50 | 5 |
| Std.[1] | 96 | 93 | 70 | 86 | 50 | 7 |
| Std.[1] |  |  | 22 | 0 | 36 | 8 |
| Std.[1] | 84 | 31 | 41 | 24 | 58 | 9 |
| Std.[1] | 88 | 71 | 29 | 50 | 56 | 10 |
| Std.[1] | 84 | 70 | 36 | 18 | 44 | 11 |
| Std.[1] | 95 | 69 | 64 | 38 | 42 | 12 |
| Std.[1] | 80 | 55 | 53 | 25 | 64 | 13 |
| Std.[1] | 55 | 27 | 30 | 15 | 66 | 16 |
| Std.[1] | 74 | 34 | 21 | 24 | 58 | 18 |
| Std.[1] | 68 | 12 | 12 | 4 | 50 | 20 |
| Std.[1] | 64 | 59 | 24 | 0 | 34 | 22 |
| Std.[1] | 94 | 83 | 76 | 58 | 26 | 24 |
| Std.[1] | 96 | 85 | 67 | 53 | 30 | 26 |
| Std.[1] | 85 | 57 | 38 | 10 | 42 | 28 |
| Std.[1] | 96 | 60 | 43 | 5 | 42 | 30 |
| Std.[1] | 77 | 54 | 25 | 17 | 48 | 32 |
| Std.[1] | 73 | 54 | 38 | 32 | 48 | 33 |
| Std.[1] | 93 | 66 | 46 | 32 | 56 | 34 |
| Std.[1] | 75 | 47 | 42 |  | 76 | 35 |
| Std.[1] | 81 | 68 | 42 |  | 38 | 36 |
| Std.[1] | 93 | 83 | 69 |  | 64 | 37 |
| Std.[1] | 80 | 43 | 17 |  | 46 | 38 |
| Std.[1] | 97 | 92 | 83 |  | 42 | 39 |
| Std.[1] |  | 73 | 62 | 71 | 52 | 40 |
| Std.[1] |  | 94 | 77 | 36 | 44 | 41 |
| Std.[1] |  | 75 | 56 | 65 | 46 | 42 |
| Std.[1] |  | 96 | 91 | 87 | 34 | 43 |
| Std.[1] |  | 96 | 91 | 77 | 28 | 44 |
| average | 81 | 62 | 46 | 34 | 47 |  |
| Std.[2] | 86 | 64 | 32 | 28 | 50 | 5 |
| Std.[2] | 93 | 82 | 54 | 60 | 50 | 7 |
| Std.[2] |  |  | 50 | 0 | 36 | 8 |
| Std.[2] | 45 | 38 | 24 | 10 | 58 | 9 |
| Std.[2] | 58 | 26 | 13 |  | 76 | 35 |
| average | 71 | 53 | 35 | 25 | 54 | 13 |
| 5 |  | 44 | 32 | 20 | 50 | 3 |
| 5 | 84 | 72 | 60 | 8 | 50 | 5 |
| 5 | 91 | 54 | 64 | 62 | 50 | 7 |
| 3 | 53 | 6 | 0 | 0 | 51 | 2 |
| 3 |  | 72 | 64 | 58 | 50 | 3 |
| 3 | 80 | 72 | 80 | 74 | 50 | 5 |
| 3 | 92 | 66 | 60 | 74 | 50 | 7 |
| 16 | 96 | 95 | 89 | 50 | 30 | 26 |
| 17 | 100 | 99 | 83 | 86 | 30 | 26 |
| 19 | 92 | 64 | 67 | 48 | 42 | 28 |

TABLE 5-continued

| EX.NO. | % control of root rot | | | | % disease | |
|---|---|---|---|---|---|---|
| | 1 g/kg | 0.5 | 0.25 | 0.125 | non TRT | test # |
| 20 | 99 | 90 | 76 | 62 | 42 | 28 |
| 22 | 83 | 67 | 62 | 14 | 42 | 30 |
| 23 | 100 | 100 | 100 | 48 | 42 | 30 |
| 41 | 87 | 83 | 46 | 50 | 48 | 32 |
| 42 | 98 | 99 | 80 | 73 | 56 | 34 |
| 21 | 100 | 100 | 95 |  | 42 | 39 |
| 7 | 50 | 39 | 45 |  | 38 | 36 |
| 4 | 91 | 86 | 81 |  | 38 | 36 |
| 43 | 98 | 90 | 82 | 61 | 56 | 34 |
| 18 | 95 | 95 | 89 | 77 | 56 | 34 |
| 11 | 38 | 34 | 41 | 14 | 58 | 18 |
| 1 | 92 | 71 | 71 | 50 | 42 | 12 |
| 1 | 72 | 74 | 70 |  | 76 | 35 |
| 6 | 78 | 69 | 69 | 38 | 42 | 12 |
| 6 | 88 | 71 | 61 |  | 76 | 35 |
| 15 | 52 | 43 | 33 | 38 | 42 | 12 |
| 9 | 43 | 52 | 48 | 14 | 42 | 12 |
| 2 | 82 | 70 | 55 | 30 | 66 | 16 |
| 2 | 78 | 63 | 47 |  | 76 | 35 |
| 24 |  | 47 | 9 | 0 | 34 | 43 |
| 26 |  | 18 | 17 | 0 | 34 | 43 |
| 25 |  | 44 | 29 | 64 | 34 | 43 |
| 13 | 52 | 60 | 62 |  | 42 | 39 |
| 12 | 88 | 79 | 67 |  | 42 | 39 |
| 29 |  | 27 | 73 | 12 | 52 | 40 |
| 31 |  | 50 | 54 | 52 | 52 | 40 |
| 30 |  | 71 | 23 | 50 | 52 | 40 |
| 32 |  | 18 | 36 | 18 | 44 | 41 |
| 34 |  | 27 | 0 | 18 | 44 | 41 |
| 33 |  | 23 | 18 | 23 | 44 | 41 |
| 27 |  | 61 | 55 | 23 | 44 | 41 |
| 28 |  | 35 | 65 | 67 | 46 | 42 |
| 38 |  | 13 | 22 | 9 | 46 | 42 |
| 35 |  | 13 | 37 | 28 | 46 | 42 |
| 36 |  | 0 | 0 | 9 | 46 | 42 |
| 39 |  | 13 | 0 | 0 | 46 | 42 |
| 40 |  | 9 | 4 | 17 | 46 | 42 |
| 37 |  | 13 | 13 | 4 | 46 | 42 |
| Std.[3] |  |  | 0 | 0 | 36 | 8 |
| Std.[3] | 55 | 41 | 34 | 28 | 58 | 9 |
| average | 55 | 41 | 17 | 14 | 47 |  |
| 47 | 77 | 41 | 53 | 38 | 64 | 13 |
| 56 | 83 | 47 | 56 | 31 | 64 | 13 |
| 63 | 84 | 75 | 47 | 19 | 64 | 13 |
| 55 | 73 | 67 | 45 | 36 | 66 | 16 |
| 66 | 84 | 60 | 44 | 32 | 50 | 20 |
| 48 | 96 | 88 | 60 | 60 | 50 | 20 |
| 59 | 85 | 85 | 68 | 6 | 34 | 22 |
| 52 | 93 | 91 | 87 | 65 | 26 | 24 |
| 45 | 96 | 83 | 83 | 54 | 48 | 33 |
| 67 | 68 | 53 | 29 |  | 38 | 36 |

Std.[1] is 2-chloro-N-ethyl-6-(trimethylsilyl)benzamide
Std.[2] is 2-chloro-6-[(1,1-dimethylethyl)amino]-N-ethylbenzamide
Std.[3] is 2-chloro-6-(1,1-dimethylethoxy)-N-ethylbenzamide Field Tests The compounds of Examples 1–73 are combined with various adjuvants, carriers, and other additives and mixed with wheat and barley seed at rates of from 0.01 to 50 g active ingredient per kg of seed which reduce the incidence of Gg in previously infested fields compared to check fields seeded with untreated seed.

| Composition Examples | Wt. Pct. |
|---|---|
| Suspension Concentrate: | |
| Compound No. 17 | 48.900 |
| polyoxypropylene-polyoxyethylene block | 2.550 |

-continued

| Composition Examples | Wt. Pct. |
| --- | --- |
| copolymer | |
| Sodium Lignin Sulfonate | 2.040 |
| 10% Dimethylpolysiloxane Emulsion | 1.020 |
| 1% Xanthan gum solution | 0.990 |
| Water | 43.250 |
| Emulsifiable Concentrate: | |
| Compound No. 19 | 13.5 |
| Ethoxylated sorbitan (20EO) | 5.0 |
| C9 Aromatics | 81.5 |
| Wettable Powder: | |
| Compound No. 20 | 75.0 |
| Sodium lignin sulfonate | 3.0 |
| Sodium N-methyl-N-oleyl-taurate | 1.0 |
| Kaolinite clay | 11.0 |
| Granule: | |
| Compound No. 21 | 1.0 |
| Propylene glycol | 5.0 |
| Montmorillonite (24/48 mesh) | 94.0 |
| Dust: Wt. Pct, | |
| Compound No. 15 | 50.0 |
| Graphite | 10.0 |
| Kaolinite clay | 40.0 |

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

We claim:

1. A compound of the formula (I)

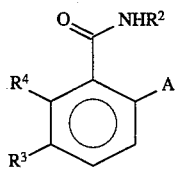

wherein $R^2$ is ethyl, iso-propyl, propyl or allyl;

A is $N(CH_3)_{1-n}H_nR^5$ or $OR^6$ wherein n is 0 or 1, $R^5$ is $(CH_3)_m(CH_3CH_2)_{3-m}C$, 1-methyl-1-cyclopentyl, 1-methyl-1-cyclohexyl or 2,3-dimethyl-2-butyl wherein m is 0, 1, 2 or 3 and $R^6$ is independently $R^5$ or 2,3,3-trimethyl-2-butyl;

$R^3$ is H or independently $R^4$; and $R^4$ is halo or $CH_3$;

with the proviso that when A is $N(CH_3)_{1-n}H_nR^5$ where n is 0 or 1, if $R^3$ is H and $R^5$ is 1-methyl-1-cyclohexyl or $(CH_3)_m(CH_3CH_2)_{3-m}C$, where m is 0 or 3, or if $R^3$ is halo and $R^5$ is $(CH_3)_m(CH_3CH_2)_{3-m}C$, where m is 3, then $R^2$ cannot be ethyl;

and with the proviso that when A is $OR^6$ then m is equal to or less than 2, and if $R^3$ is H or halo and $R^2$ is ethyl or isopropyl, then $R^6$ is $(CH_3)_m(CH_3CH_2)_{3-m}C$ where m is 1; or an agronomic salt thereof.

2. A compound of claim 1 wherein A is $N(CH_3)_{1-n}H_nC(CH_3)_m(CH_2CH_3)_{3-m}$ wherein n is 0 or 1; m is 1,2 or 3; $R^2$ is ethyl, propyl or allyl; $R^3$ is methyl; and $R^4$ is chloro.

3. A compound of claim 1 wherein A is $OC(CH_3)_m(CH_2CH_3)_{3-m}$ wherein m is 1 or 2, or $OC(CH_3)_2CH(CH_3)_2$; $R^2$ is allyl; $R^3$ is H or methyl; and $R^4$ is chloro.

4. A compound of claim 1 which is N-ethyl 2-[(1,1-diethylethyl)amino]-6-chlorobenzamide, N-ethyl 2-[(1,1,2-trimethylpropyl)amino]-6-chlorobenzamide, N-propyl 2-[(1,1-dimethylpropyl)amino]-6-chlorobenzamide or N-allyl 2-[(1,1-dimethylethyl)amino]-6-chlorobenzamide.

5. A composition for the control of Take-all disease in plants by treating seeds of said plants or by treating the soil for said plants comprising an effective amount of the compound of claim 1 together with an agronomically acceptable carrier.

6. A method of controlling Take-all disease in plants which comprises treating seeds of said plants or treating the soil for said plants with an effective amount of a compound of claim 1.

7. A compound of claim 1 which is N-allyl 2-[(1,1-dimethylethyl)amino]-5-methyl-6-chlorobenzamide.

8. A compound of claim 1 which is N-ethyl 2-[(1,1-dimethylpropyl)amino]-5-methyl-6-chlorobenzamide.

9. A compound of claim 1 which is N-allyl 2-[(1,1-dimethylpropyl)amino]-5-methyl-6-chlorobenzamide.

10. A compound of claim 1 which is N-propyl 2-[(1,1-dimethylpropyl)amino]-5-methyl-6-chlorobenzamide.

11. A compound of claim 1 which is N-propyl 2-[(1,1-diethylethyl)oxy]-6-methyl-6-chlorobenzamide.

12. A compound of claim 1 which is N-allyl 2-[(1,1,2-trimethylpropyl)oxy]-6-chlorobenzamide.

* * * * *